United States Patent [19]

Miller et al.

[11] Patent Number: 5,243,098
[45] Date of Patent: Sep. 7, 1993

[54] CONVERSION OF METHANE TO METHANOL

[75] Inventors: Jorge P. Miller; Miguel Kling, both of Bogota, Colombia

[73] Assignee: Energia Andina Ltd., New York, N.Y.

[21] Appl. No.: 971,899

[22] Filed: Nov. 4, 1992

[51] Int. Cl.[5] .................... C07C 29/124; C07C 31/04; C07C 31/08; C07C 31/10
[52] U.S. Cl. ........................................ 568/893; 422/139
[58] Field of Search ........................................ 568/893

[56] References Cited

U.S. PATENT DOCUMENTS

| | | | |
|---|---|---|---|
| 1,086,381 | 2/1914 | Masland | 568/893 |
| 3,140,322 | 7/1964 | Frilette et al. | 568/893 |
| 3,172,915 | 3/1965 | Borkowski et al. | 568/893 |
| 4,523,040 | 6/1985 | Olah | 568/893 |

Primary Examiner—Joseph E. Evans
Attorney, Agent, or Firm—Jacobson, Price, Holman & Stern

[57] ABSTRACT

Lower alkanols are prepared from corresponding alkanes by reacting the lower alkane with a metal halide to produce a lower alkyl halide which, in turn, is reacted with magnesium oxide to form the corresponding lower alkanol. A continuous fluidized-bed system is provided for conducting the necessary reactions.

8 Claims, 1 Drawing Sheet

CONVERSION OF METHANE TO METHANOL

FIELD OF THE INVENTION

Methane is reacted with a metal chloride to produce methyl chloride. Reacting the obtained methyl chloride with magnesium oxide and steam yields methanol.

BACKGROUND

Methane has previously been chlorinated with gaseous chlorine or subjected to oxychlorination with oxygen and hydrochloric acid to form methyl chloride together with other chlorides, such as dichloromethane, trichloromethane and carbon tetrachloride. In the halogenation of methane by either method, hydrochloric acid is produced. Such hydrochloric acid must be recovered, dehydrated by azeotropic distillation and recycled.

Reduced chloromethanes are then hydrolyzed in vapor phase to methanol, formaldehyde, formic acid, carbon dioxide and hydrochloric acid. Resulting compositions depend on the chlorination selectivity to methyl chloride and to other chlorides. Corrosion and problems involved with handling chlorine and hydrochloric acid are substantial.

SUMMARY OF THE INVENTION

An object of the invention is to overcome or eliminate previously-encountered problems and to obtain a simplified process for converting an alkane to the corresponding alkanol. The method is based on the formation of an alkyl chloride and its hydration to the corresponding alcohol.

According to this process, methane (the preferred alkane) is reacted with a metal chloride (metallic chloride), wherein the metal is in the higher of two possible valence states, to form methyl chloride, the corresponding metal chloride (metallous chloride), wherein the metal is in the lower of two possible valence states, and hydrochloric acid. The obtained methyl chloride and hydrochloric acid are reacted with magnesium oxide to form methyl alcohol and magnesium chloride hydrate. The obtained metallous chloride is reacted with hydrochloric acid and oxygen to form metallic chloride, and the magnesium chloride hydrate is converted to magnesium oxide and hydrochloric acid.

DETAILS

Figure 1:
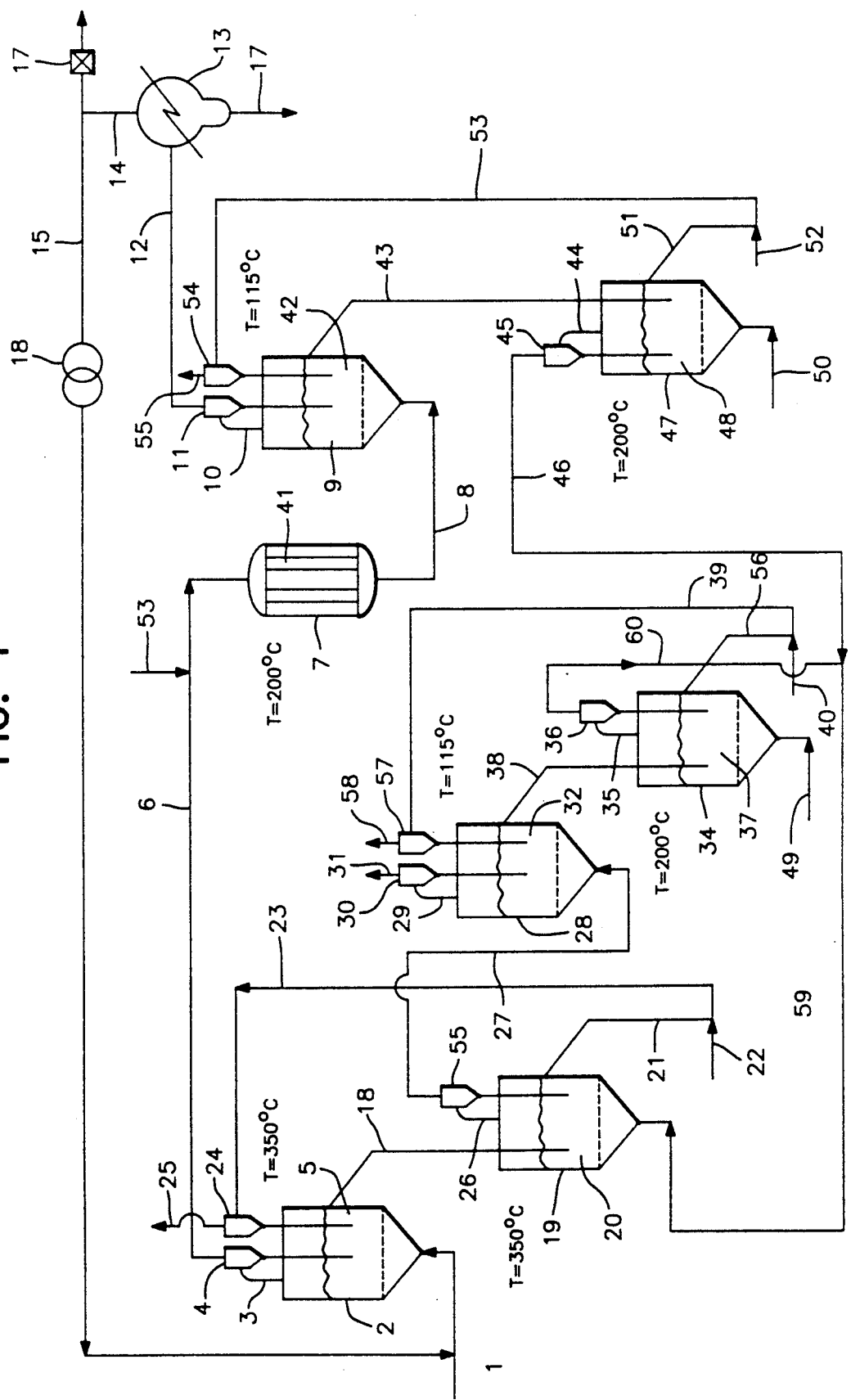
FIG. 1 is a flow diagram depicting one embodiment of the claimed process.

Methane is reacted with a metal chloride which is capable of chlorinating methane. The metal is one which concurrently reduces its valence to a lower state. For example, cupric chloride reacts with methane to form methyl chloride, cuprous chloride and hydrochloric acid, according to reaction (I)

$$2CuCl_2 + CH_4 \rightarrow 2CuCl + CH_3Cl + HCl \quad (I)$$

The obtained methyl chloride and hydrochloric acid are next reacted with steam and a catalyst containing magnesium oxide, according to reaction scheme (II)

$$H_2O + CH_3Cl + HCl + MgO \rightarrow CH_3OH + MgCl_2 \cdot H_2O \quad (II)$$

Air and oxygen are passed countercurrent through the magnesium chloride to recover hydrochloric acid according to reaction scheme (III)

$$MgCl_2 \cdot xH_2O \rightarrow MgO + 2HCl \quad (III)$$

and then through the cuprous chloride to reform cupric chloride according to reaction scheme (IV)

$$2HCl + \tfrac{1}{2}O_2 + 2CuCl \rightarrow 2CuCl_2 + H_2O \quad (IV)$$

Reaction (I) is advantageously carried out at temperatures between 300° C. and 360° C., at which temperatures there is no formation of chlorine by decomposition of cupric chloride. Such decomposition takes place at 993° C. to yield chlorine. By keeping the temperature low, the possibility of overchlorination of the methyl chloride to higher chlorides is minimized.

Reaction (II) is advantageously conducted at 200° C. or less in order to avoid adsorbing chlorides and to release them according to the law of mass action.

Reaction (III) is advantageously carried out at about 200° C., and reaction (IV) is advantageously carried out within the approximate range of from 300° C. to 380° C.

The preferred method is a continuous process, using fluidized-bed reactors. However, fluidized bed reactors are not necessary, and batch reactions can be employed. Instead of a metal chloride, such as copper chloride, in reaction (I), a mixture can be employed. The preferred mixture is one of cupric chloride, cuprous chloride and magnesium oxide. This particular mixture is preferably used for chlorination of methane because, by diluting the copper chloride with magnesium oxide, less higher methyl chlorides are formed. Also, when reoxidizing in the presence of hydrochloric acid, the magnesium chloride formed reacts with any copper oxide formed to produce copper chloride. Magnesium oxide also serves to increase porosity.

$$MgCl_2 + CuO \rightarrow MgO + CuCl_2 \quad (V)$$

Excess cuprous chloride adsorbs any formed chlorine.

$$CuCl + \tfrac{1}{2}Cl_2 \rightarrow CuCl_2 \quad (VI)$$

Instead of reacting methyl chloride with magnesium oxide in reaction (II), a magnesium zeolite can be used to hydrolyze the methyl chloride to methanol and hydrochloric acid; at 200° C. the hydrochloric acid is next adsorbed by magnesium oxide. At temperatures in excess of 115° C., $MgCl_2 \cdot 4H_2O$ is formed, completely adsorbing all of the hydrochloric acid, which can be recovered by heating to 200° C., while passing air therethrough.

The mechanism and kinetics of the thermal decomposition of magnesium chloride hydrates have been reported ("Kirk-Othmer Encyclopedia of Chemical Technology", Vol. 14–623, Third Edition). The reactions which are reversible take place in stages as shown.

95° C.–115° C. $MgCl_2 \cdot 6H_2O \rightleftharpoons MgCl_2 \cdot 4H_2O + 2H_2O$ 135° C.–180° C. $MgCl_2 \cdot 4H_2O \rightleftharpoons Mg(OH) + HCl + 3H_2O$ 186° C.–230° C. $MgCl_2 \cdot H_2O \rightleftharpoons Mg(OH)Cl + HCl$ 230° C. $Mg(OH)Cl \rightleftharpoons MgO + HCl$ Advantage is taken of these properties of magnesium chloride hydrates to adsorb and recover hydrochloric acid.

The exceedingly high conversion of methyl chloride to methyl alcohol (practically 100%), by the magnesium form of the zeolite (Mg $Z_2$), can be attributed to the following reactions:

$$MgZ_2 + 2CH_3Cl \rightarrow MgCl_2 + 2CH_3Z$$

$$CH_3Z + H_2O \rightarrow HZ + CH_3OH$$

and $$MgCl_2 + H_2O \rightarrow Mg(OH)_2 + 2HCl$$

$$Mg(OH)_2 + 2HZ \rightarrow MgZ_2 + 2H_2O$$

In this case the magnesium zeolite acts like a catalyst.

With reference to FIG. 1, which depicts a typical continuous process using fluidized reactors, methane is introduced to fluid bed fluidizer 2 through line 1, where it reacts with cupric chloride contained in fluidized reactant 5, composed of a mixture of magnesium oxide, cupric chloride and cuprous chloride. (Alternatively, cupric bromide and cuprous bromide can be used). The reacted gas, comprising mostly hydrochloric acid, methyl chloride and excess methane, flows through line 3 to cyclone 4, which returns dust to reactor 2. Gas, leaving cyclone 4 through line 6, enters reactor 7, which contains catalyst (magnesium zeolite) 41, together with steam provided through line 53. Reacted gases, comprising methyl alcohol, hydrochloric acid and excess methane, leave reactor 7 through line 8, which delivers them to fluidizer 9, containing magnesium oxide 42, which adsorbs all the hydrochloric acid.

Gases leaving fluidizer 9 through line 10 to cyclone 11, which returns dust to fluidizer 9, contain methyl alcohol and excess methane. These gases are led through line 12 to condenser 13, where methyl alcohol is condensed and leaves condenser 13 through line 17.

Non-condensed methane leaves condenser 13 through line 14 to bleed valve 17 and through line 15 to compressor 16, which recirculates excess methane to line 1.

Spent reactant 5 from fluidizer 2 flows through line 18 to fluidizer 19, where it meets a flow of gas containing air and hydrochloric acid; cuprous chloride therein is regenerated back to cupric form.

Regenerated reagent 20 flows through line 21, where it meets conveying gas air 22, which lifts it through line 23 to cyclone 24, where conveying gas (air) is exhausted through line 25 to the atmosphere and reagent 5 is delivered by cyclone 24 to fluidizer 2.

Gases from fluidizer 19, containing possible traces of hydrochloric acid, are led through line 26 to cyclone 55, returning dust to fluidizer 19 and delivering gases through line 27 to fluidizer 28, which contains magnesium oxide 32, which adsorbs all traces of hydrochloric acid. The purified gas is bled to the atmosphere through line 29 and cyclone 30, which returns dust to fluidizer 28 and exhausts clean gas, free of pollution, through line 31.

Spent magnesium oxide 32 leaves fluidizer 28 through line 38, which delivers it to fluidizer 34, where it meets a flow of air, which regenerates the spent magnesium oxide 37. Regenerated magnesium oxide is conducted through line 56, where a conveying gas 40 lifts it through line 39 to cyclone 57. Conveying gas is exhausted through line 58 to the atmosphere, and regenerated magnesium oxide is delivered to fluidizer 28. Gases leaving fluidizer 34, containing air and hydrochloric acid, are led through line 35 to cyclone 36, where dust is returned to fluidizer 34, and gases are led through line 60 to line 59.

Spent magnesium oxide 42 leaves fluidizer 9 through line 43, which delivers it to fluidizer 47, where it meets a flow of air, introduced through line 50, which regenerates the spent magnesium oxide 48. Regenerated magnesium oxide flows through line 51, where it meets a conveying gas (air) 52, which lifts it to cyclone 54 through line 53. Conveying gas is exhausted through line 55, and cyclone 54 delivers regenerated magnesium oxide to fluidizer 9.

Gases leaving fluidizer 47, containing hydrochloric acid and air, are delivered through line 44 to cyclone 45, where dust is returned to fluidizer 47, and gases are led through line 46 to line 59 and, together with gases from line 60, enter fluidizer 19.

Air enters fluidizer 34 through line 49; air enters fluidizer 47 through line 50.

Temperatures indicated in FIG. 1 are indicative. Reactant 5 is made, e.g., by mixing cuprous chloride, cupric chloride and magnesium oxide, the molar proportions suggested are:

cupric chloride 1 mole cuprous chloride 0.1 mole magnesium oxide 2 moles

The reagent is advantageously made as follows:

1.1 mole of cupric chloride is dissolved in water to saturation. 2 moles of magnesium oxide are added. The mixture is evaporated to dryness and granulated.

The granulated product is then reduced with methane or hydrogen until 0.1 mole of copper chloride is reduced to cuprous chloride. When regenerating the reagent, cuprous chloride must always be present.

Magnesium oxide serves to tone down the activity of the cupric chloride. Other diluent materials can be used in combination with magnesium oxide (aluminum oxide, silica, fullers earth, etc.).

When conversion per pass is limited to less than 20%, overchlorination of the methane is limited to less than 1%. Increasing magnesium oxide in the reagent also has the same effect.

Magnesium zeolite catalyst is preferably prepared as follows: Type A or Type X zeolite, as defined in "Kirk-Othmer Encyclopedia of Chemical Technology", 3d Edition, Vol. 15, Page 665, is placed in a column, and a solution of soluble magnesium salt (sulfate, nitrate, etc.) is passed through the zeolite, whereby sodium is exchanged for magnesium. The zeolite in the magnesium form is then washed and dried, ready for use. The process is well known ("Kirk-Othmer Encyclopedia of Chemical Technology", 3d Edition, Vol. 13, page 678, etc.).

Although the preceding illustration has been made with copper chlorides, such chlorides are optionally replaced with bromides. Also, methane is optionally replaced with ethane, propane or n-butane to produce corresponding alcohols.

The invention and its advantages are readily understood from the preceding description. It is apparent that various changes may be made in the process, in the system and in the compositions, without departing from the spirit and the scope of the invention or sacrificing its material advantages. The process, systems and products hereinbefore described are merely illustrative of preferred embodiments of the invention.

What is claimed is:

1. A process for producing a lower alkanol from the corresponding lower alkane which comprises:
   a) reacting the lower alkane with a metal halide (metallic halide), wherein the metal is in the higher of two possible valence states, to form the corresponding lower alkyl halide, the corresponding metal halide (metallous halide), wherein the metal is in the lower of two possible valence states, and hydrohalic acid; and
   b) reacting the obtained lower alkyl halide and hydrohalic acid with magnesium oxide to form the corresponding lower alkanol and magnesium halide hydrate.

2. A process of claim 1 which further comprises:
   c) reacting the metallous halide with hydrohalic acid and oxygen to form metallic halide; and
   d) converting the magnesium halide hydrate to magnesium oxide and hydrohalic acid.

3. A process of claim 2 wherein the metal halide is copper chloride.

4. A process of claim 3 substantially conducted in a fluidized bed.

5. A process for producing methanol from methane which comprises:
   a) reacting methane with a metal chloride (metallic chloride), wherein the metal is in the higher of two possible valence states, to form methyl chloride, the corresponding metal chloride (metallous chloride), wherein the metal is in the lower of two possible valence states, and hydrochloric acid;
   b) passing the methyl chloride and hydrochloric acid obtained from step (a), together with steam, through a magnesium zeolite catalyst to form methyl alcohol and hydrochloric acid;
   c) reacting the methyl alcohol and hydrochloric acid obtained from step (b) with magnesium oxide to obtain methyl alcohol and magnesium chloride hydrate; and
   d) converting the magnesium chloride hydrate to magnesium oxide and hydrochloric acid.

6. A process of claim 5 wherein the metal chloride is copper chloride.

7. A process of claim 6 substantially conducted in a fluidized bed.

8. A process of claim 7 which comprises:
   a) reacting methane with cupric chloride in a fluidized bed comprising a mixture of magnesium oxide, cupric chloride and cuprous chloride to form a combination of gases comprising hydrochloric acid, methyl chloride and unreacted methane;
   b) passing the combination of gases and steam through a magnesium zeolite catalyst to obtain an admixture of methyl alcohol, hydrochloric acid and methane;
   c) passing the admixture through a fluidized bed containing magnesium oxide, which adsorbs all of the hydrochloric acid;
   d) condensing the methyl alcohol from the remaining combination of methyl alcohol and methane; and
   e) recirculating the methane to step (a).

* * * * *